US012433827B2

(12) United States Patent
Kamps et al.

(10) Patent No.: US 12,433,827 B2
(45) Date of Patent: Oct. 7, 2025

(54) FOAMABLE CLEANSING COMPOSITIONS

(71) Applicant: DEB IP LIMITED, Denby (GB)

(72) Inventors: Nicole Kamps, Denby (GB); Marcel Veeger, Denby (GB); Astrid Thiemann, Denby (GB); Caroline Fellows, Denby (GB)

(73) Assignee: DEB IP LIMITED, Derbyshire (GB)

( * ) Notice: Subject to any disclaimer, the term of this patent is extended or adjusted under 35 U.S.C. 154(b) by 774 days.

(21) Appl. No.: 17/526,239

(22) Filed: Nov. 15, 2021

(65) Prior Publication Data

US 2022/0175628 A1 Jun. 9, 2022

Related U.S. Application Data

(63) Continuation-in-part of application No. 16/485,246, filed as application No. PCT/GB2018/050455 on Feb. 22, 2018, now abandoned.

(30) Foreign Application Priority Data

Feb. 23, 2017 (GB) ..................................... 1702905

(51) Int. Cl.
*C11D 1/66* (2006.01)
*A61K 8/04* (2006.01)
(Continued)

(52) U.S. Cl.
CPC ................ *A61K 8/046* (2013.01); *A61K 8/37* (2013.01); *A61K 8/42* (2013.01); *A61Q 19/10* (2013.01);
(Continued)

(58) Field of Classification Search
CPC .. C11D 1/02; C11D 1/14; C11D 1/662; C11D 1/90; C11D 1/94; C11D 1/75;
(Continued)

(56) References Cited

U.S. PATENT DOCUMENTS 5,712,235 A 1/1998 Nieendick
6,082,586 A 7/2000 Banks
(Continued)

FOREIGN PATENT DOCUMENTS

CN 103038326 A 4/2013
CN 105263582 A 1/2016
(Continued)

OTHER PUBLICATIONS

Wei, Chao et al., "Pharmaceutics", Henan Science and Technology Press, with English Translation, 9 pages.
(Continued)

*Primary Examiner* — Gregory R Delcotto

(57) ABSTRACT

The invention describes a foamable skin and hand cleansing composition including the following components in percentages of the composition:

a) 0.1 to 5% by weight of at least one emulsifier;
b) 0.5 to 7% by weight of at least one oil;
c) 0 to 10% by weight of at least one hydrophobic emollient
d) 5 to 20% by weight of at least one surfactant used as a soiling remover;
e) 0.5 to 12% by weight of at least one fatty acid glucamide;
f) 1 to 8% by weight of at least one surfactant used as a foamer;
g) 0 to 1% by weight of at least one preservative;
h) 0 to 1% by weight of a pH modifier;
i) 0 to 10% by weight of one or more auxiliaries or additives; and
j) water to make up 100% by weight.

17 Claims, 3 Drawing Sheets

(51) Int. Cl.

| | |
|---|---|
| ***A61K 8/37*** | (2006.01) |
| ***A61K 8/42*** | (2006.01) |
| ***A61Q 19/10*** | (2006.01) |
| ***C11D 1/02*** | (2006.01) |
| ***C11D 1/14*** | (2006.01) |
| ***C11D 1/75*** | (2006.01) |
| ***C11D 1/90*** | (2006.01) |
| ***C11D 1/94*** | (2006.01) |
| ***C11D 3/20*** | (2006.01) |
| ***C11D 3/22*** | (2006.01) |
| ***C11D 3/26*** | (2006.01) |
| ***C11D 3/30*** | (2006.01) |
| ***C11D 3/32*** | (2006.01) |
| ***C11D 17/04*** | (2006.01) |

(52) U.S. Cl.

CPC .................. *C11D 1/02* (2013.01); *C11D 1/14* (2013.01); *C11D 1/662* (2013.01); *C11D 1/75* (2013.01); *C11D 1/90* (2013.01); *C11D 1/94* (2013.01); *C11D 3/2068* (2013.01); *C11D 3/22* (2013.01); *C11D 3/222* (2013.01); *C11D 3/26* (2013.01); *C11D 3/30* (2013.01); *C11D 17/046* (2013.01); *A61K 2800/87* (2013.01)

(58) Field of Classification Search

CPC ......... C11D 3/2068; C11D 3/22; C11D 3/222; C11D 3/26; C11D 3/30; C11D 17/046

USPC ....... 510/123, 125, 126, 127, 130, 136, 137, 510/138, 470, 505, 506

See application file for complete search history.

(56) References Cited

U.S. PATENT DOCUMENTS

| | | | | |
|---|---|---|---|---|
| 2010/0172848 | A1 | 7/2010 | Modak | |
| 2012/0010115 | A1 | 1/2012 | Mitchell | |
| 2012/0124724 | A1 | 5/2012 | Lapointe | |
| 2012/0214724 | A1* | 8/2012 | Scheibel | A61Q 19/10 510/447 |
| 2014/0242018 | A1 | 8/2014 | Zasloff | |
| 2015/0125403 | A1 | 5/2015 | Joerger | |
| 2015/0125415 | A1 | 5/2015 | Klug et al. | |
| 2015/0141508 | A1 | 5/2015 | Klug et al. | |
| 2016/0000094 | A1 | 1/2016 | Modak | |
| 2016/0074310 | A1 | 3/2016 | Klug et al. | |
| 2017/0156550 | A1* | 6/2017 | Ciavarella | F04B 45/043 |
| 2018/0289223 | A1* | 10/2018 | Harris | F04B 23/02 |

FOREIGN PATENT DOCUMENTS

| | | | | |
|---|---|---|---|---|
| CN | 105531000 | A | 4/2016 | |
| DE | 19934836 | C1 | 7/2000 | |
| EP | 0784465 | B1 | 6/1999 | |
| EP | 1072615 | A1 | 1/2001 | |
| JP | 11505837 | A | 5/1999 | |
| JP | 2004002329 | A1 | 1/2004 | |
| JP | 2010520258 | A | 6/2010 | |
| JP | 2015518028 | A | 6/2015 | |
| JP | 2016510611 | A | 4/2016 | |
| JP | 2017520283 | A | 7/2017 | |
| WO | 9610386 | A1 | 4/1996 | |
| WO | 9637592 | A1 | 11/1996 | |
| WO | WO-9949769 | A1 * | 10/1999 | A47K 5/14 |
| WO | 2008107453 | A2 | 9/2008 | |
| WO | 2012021130 | A1 | 2/2012 | |
| WO | 2013178697 | A2 | 12/2013 | |
| WO | 2014123916 | A1 | 8/2014 | |
| WO | 2014138958 | A1 | 9/2014 | |
| WO | 2014170025 | A1 | 10/2014 | |
| WO | 2015161018 | A1 | 10/2015 | |
| WO | 2016179503 | A1 | 11/2016 | |
| WO | WO-2017087930 | A1 * | 5/2017 | A47K 5/1208 |
| WO | WO-2017139727 | A1 * | 8/2017 | A47K 5/14 |

OTHER PUBLICATIONS

Zhang, Jingyun, "Practical Cosmetology Pharmacology", Chinese Traditional Medicine Press, with English Translation, 6 pages.

Wang, Xuemei, "Cosmtics, Health and Beauty Industry", Anhui University Press, with English Translation, 5 pages.

Written Opinion for PCT/GB2018/050455, dated Feb. 22, 2018, 12 pages.

Search Report for GB1702905.9, dated Nov. 27, 2017, 6 pages.

Japan Office Action dated Oct. 26, 2021, for Japan Application 2019-545315, filed Oct. 22, 2021, with English Translation, 17 pages.

* cited by examiner

FOAMABLE CLEANSING COMPOSITIONS

CROSS-REFERENCE TO RELATED APPLICATIONS

This application is a national stage entry of International Application no. PCT/GB2018/050455, filed on Feb. 22, 2018, which claims priority to United Kingdom Patent Application no. 1702905.9, filed on Feb. 23, 2017.

BACKGROUND OF THE INVENTION

Field of the Invention

The invention relates to foamable skin and hand cleansing compositions, especially to those adapted to be used in combination with inverted air pumps for producing a foamed product.

Brief Discussion of Prior Art

Liquid skin and hand cleansing formulations are generally known in the art. They are conventionally provided in containers that are poured or have pumps to pump the liquid compositions onto the skin to be cleaned. Such liquid soaps often have very good cleaning efficiency.

Formulations which are foamed before being placed on the skin or hands are also generally known in the art. Foams tend to be much easier to spread than the corresponding liquid and in addition there is much less waste due to splashing or run off since the foam has a much higher surface tension than the liquid. One problem associated with foams compared with liquid soaps is they tend to have a lower cleaning efficiency. However, foams have a much higher surface area than unfoamed liquid, so if the cleaning efficiency of the foam can be improved, it is possible to produce foams with the same cleaning power, as obtained with un-foamed liquid, but which require much less of the initial liquid to be used.

A number of cleansing formulations use a combination of oils and emulsifiers to assist in the removal of dirt from the skin or hands to be treated. The Applicant decided to try and produce such an oil based cleansing formulation which is able to be foamed.

Foaming pumps are generally known in the art. They are usually upright, in which the foamable liquid is placed within a container such as a bottle. A pumping unit is attached to the top of the bottle and comprises a dispenser which is pumped downwards towards the bottle and forces air through the liquid to cause foam to be dispensed from the dispenser onto the skin or hands. When the Applicant tried to produce formulations with such upright pumps, they were able to produce suitable foams by the addition of conventional washing additives such as lauramine oxide and betaines.

Inverted pumps are also known in which the foam dispenser is provided at the bottom of a container within a dispenser placed on, for example, the wall of a room. Such dispensers have the advantage that the foamable liquid does not need to be pumped from the bottom of a storage container by a tube extending down to the bottom of the container. This removes a problem associated with such upright containers that, as the liquid is depleted, greater force must be exerted in the pumping procedure in order to raise the liquid from the bottom of the container during dispensing of the liquid. Inverted foam dispensers are shown in, for example, WO 99/49769 and WO 2014/138958.

Examples of the inverted foaming dispenses as discussed in WO 2014/138958 are shown in FIGS. 2-3. With continued reference to FIGS. 2-3, dispenser 10 includes a foaming assembly 12 connected to a liquid container. Such dispensers foam from the base of the dispenser, rather than a top pump foam dispenser. The foaming element and/or pump are typically at the base of a container. Foam is expelled from the base of the dispenser on activating a pump, such as a manually operated pump, to expel a foamable composition through a foaming component or element of the dispenser.

However, when the Applicant tried to use the oil and emulsifier-based cleansing formulations, in combination with conventional washing additives, they found that they were unable to obtain satisfactory quality foam from the inverted dispensers, despite the fact that the same formulations worked with conventional upright dispensers. A wide range of different additives were tried, until the Applicant unexpectedly found a class of additives which allowed a formulation to be produced, which could be used in both inverted and upright foam dispensers.

The solution to this problem was not immediately apparent as formulations comprising the washing additive without the oil were still found to have problems being dispensed from inverted dispensers. It was only when the washing additive was combined with the oil and emulsifier that the problem with the inverted dispenser was resolved.

The class of additives used to overcome the problem of using the inverted foam dispensers are known as fatty acid glucamides. These have been previously used in washing and cleaning formulations and in the cosmetics industry as surfactants. There are described generally in EP 1072615 and commercially available from Clariant GmbH, Germany under the trade name Glucotain™. They are typically produced from sugars, such as D-glucose via reaction with methylamine and hydrogenation to open out the structure of the glucose to produce glucamine. This is then reacted with, for example, a fatty acid methylester or triglyceride to produce the glucamide.

SUMMARY OF THE INVENTION

Accordingly, the invention provides a foamable skin and hand cleansing composition comprising the following components, in each cased based on the total composition of the cleaning composition:

a) 0.1 to 5% by weight of at least one emulsifier;

b) 0.5 to 7% by weight of at least one oil;

c) 0 to 10% by weight of at least one hydrophobic emollient;

d) 5 to 20% by weight of at least one surfactant used as a soiling remover;

e) 0.5 to 12% by weight of at least one fatty acid glucamide f) 1 to 8% by weight of at least one surfactant used as a foamer g) 0 to 1% by weight of at least one preservative h) 0 to 1% by weight of a pH modifier i) 0 to 10% by weight of one or more auxiliaries or additives j) water to make up 100% by weight.

The composition typically comprises 0.7 to 10%, or 1 to 5% by weight of at least one fatty acid glucamide (e). Fatty acid glucamide (e) typically has a general formula:

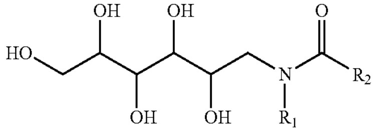

(1)

where:

$R^1$=H or a C1 to C4 alkyl, most typically H or —$CH_3$, especially —$CH_3$ $R^2$=$C_6$ to $C_{20}$ linear or branched hydrocarbon residue, most typically $C_8$ to $C_{18}$ linear or unbranched hydrocarbon residue. The hydrocarbon residue may be saturated or unsaturated.

Mixtures of the glucoamines may be used. For example, the glucamide may be a mixture of capryloyl/caproyl methyl glucamide; lauroyl/myristoyl methyl glucamide; or cocoyl methyl glucamide. Mixtures of these may also be used, for example, a mixture of cocoyl methyl glucamide and capryloyl/caproyl methyl glucamide may be used. Most typically the glucoamide is cocoyl methyl glucamide comprising fatty acid residues from coconut oil.

The oil (b) may be an alkyl fatty acid ester, most typically an isopropyl fatty acid ester or an ethylhexyl fatty acid ester. The fatty acid moiety of the ester may be a $C_6$ to $C_{20}$, such as $C_{12}$ to $C_{15}$ saturated or unsaturated fatty acid. These include, for example, saturated fatty acids and include myristic acid, palmitic acid and stearic acid and mixtures of fatty acids such as derived from rape seed oil. Most typically the alkyl moiety comprises 1-5 carbons including methyl, ethyl, propyl, butyl, isopropyl. pentyl or ethylhexyl, or is an alkyl benzoate, such as $C_{12}$ to $C_{15}$alkyl benzoate. More typically the alkyl is isopropyl or ethylhexyl, especially isopropyl. Mixtures of two or more oils may be used. Most typically the oil is isopropyl myristate or a mixture of isopropyl myristate and isopropyl palmitate. Ethylhexyl stearate may be used. The oils are typically substantially clear oils. The composition may comprise 1 to 5% by weight, or 3 to 5% by weight of the oil(s).

The emulsifier (a) may be selected from those generally known in the art including PEG-18 castor dioleate, polyglycerin 4-caproate, hydrogenated castor oil, PEG-10 glyceryl dioleate and gemini surfactants and mixtures thereof. Gemini surfactants are a family of surfactant molecules possessing more than one hydrophobic tail and hydrophilic head group. Gemini surfactants usually have better surface-active properties than corresponding conventional surfactants of equal chain length. For example, they have the hydrophobic to hydrophilic head groups connected to one another via a spacer. These are described in, for example, a review article by S. K. Hate and S. P. Moulik, Current Science, Vol 82(9) (2002) 1101-1111.

Most typically the emulsifier is PEG-18 castor oil dioleate, a Gemini surfactant or PEG 10-dioleate, especially PEG-10 dioleate or a Gemini surfactant.

Other emulsifiers that can be used are glycereth-7 caprylate/caprate (Emanon Ev-E), The composition may comprise 1 to 5% by weight of emulsifier (a) or 2 to 3% by weight.

The emollient (c) may be any suitable emollient that is also known as solubilizer known in the art, but is typically PEG-7 glyceryl cocoate. Other suitable emollients include polyglycerine 4 caprate, glycereth-2 cocoate, or PEG-6 caprylic/capric glycerides.

The emollients typically have an HLB value of at least 10 and typically at least 12

They are typically polyol esters such as polyglyceryl partial esters or polyglycerol fatty acid esters particularly preferred according to the invention are, for example, polyglyceryl-3 caprate or polyglyceryl-4 caprate, which are available from Degussa under the names TEGOSOFT® PC31 and TEGOSOFT® PC41.

Polyol esters for the purposes of the present invention are furthermore polyethylene glycol esters, such as, for example, PEG-7 glyceryl cocoate (discussed above), which is available from Croda Chemicals Europe Ltd. under the name Glycerox HE.

The composition typically comprises 8 to 15% by weight on anionic surfactant (d). The anionic surfactant may, for example, be an alkyl sulfate, such as sodium or ammonium lauryl sulfate or alkyl ether sulfate such as sodium laureth sulfate. Other suitable surfactants include Sodium alpha olefine sulfonate, N-cocoyl glutamic acid sodium salts, alkyl fatty acid isethionates, alkyl hydroxysultaine, alkylamidopropyl betaine, N-cocoyl glycine sodium salt, sulfonated and sulphated castor oils.

2-3% of foamer (f) may be used. Foamers are generally known in the art. This is typically not a silicon-containing foamer as they have been found to change the ability to paint surfaces in the automotive industry. They include, for example, cocoamidopropyl betaine, capryl/capamidopropyl betaine fatty alcohol ether carboxylic acids and carboxylates, alkanol amides and amine oxides, ethoxylated alkyl sulfosuccinates.

Up to 1% by weight of one or more preservatives (g) may be used. These are generally known in the art and include, for example, 1, 2-hexane dial, caprylyl glycol and tropolone. More typically sodium benzoate is used. The PH of the formulation may be adjusted by the addition of more or more pH modifiers, such as citric acid.

0-10% by weight, more typically 2-8% or 3-7% by weight of one or more auxiliaries or additives (i) may be used in the formulation. These are generally known to the person skilled in the art. They may include, for example, consistency regulators, fragrances, thickeners such as polymers, inorganic and organic UV photo protective filters, pigments, antioxidants, plant extracts, stabilisers and humectants. 0-1%, more typically 0-1-0.8% of a fragrance may be used. This improves the smell of the composition. Such fragrances are generally known in the art.

Typically no additional auxiliaries are added to the formulation.

Water is used to make up the composition to 100% by weight.

Typically the composition comprises 7-20% by total weight of the composition. Washing active substances is the combined weight of the surfactant, alkyl glucamide and foamer, (D, E, F.)

More typically washing additives contain 8-16 or 10-14% by weight washing additives.

The use of the compositions for skin and/or hand washing and methods of using the formulations for compositions for skin and/or hand washing are also provided.

BRIEF DESCRIPTION OF THE DRAWINGS

The invention will now be described by way of example only, with reference to the following figures.

FOAM PRODUCTION

Figure 1:
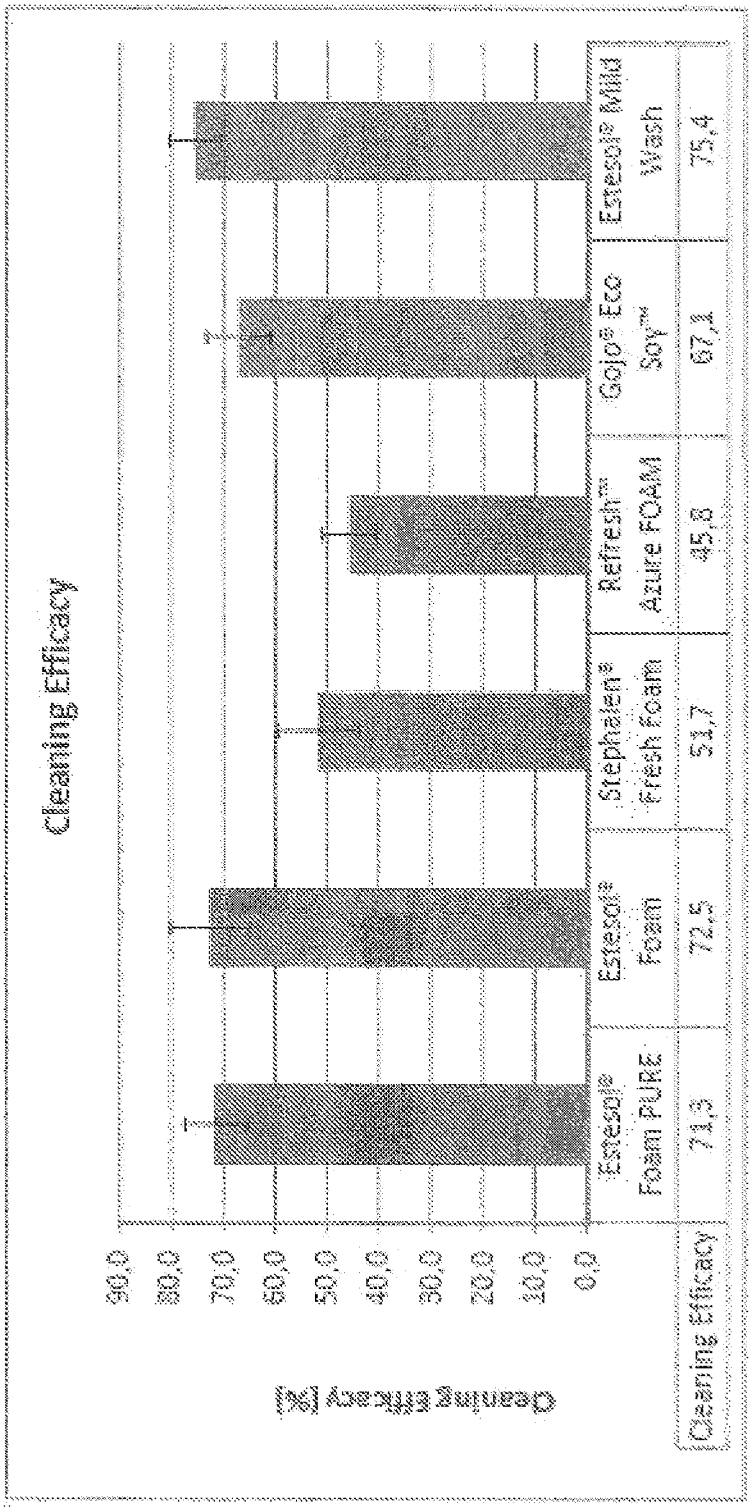
FIG. 1 shows the mean cleaning efficiencies of two foams made in accordance with the invention (Estesol Foam Pure and Estesol Foam) in comparison with Stephalen™ Flash Foam and Refresh™ Azure Foam, and in comparison with two liquid cleansers; GojoEco Soy™ and Estesol™ Mild Wash.
Figure 2:
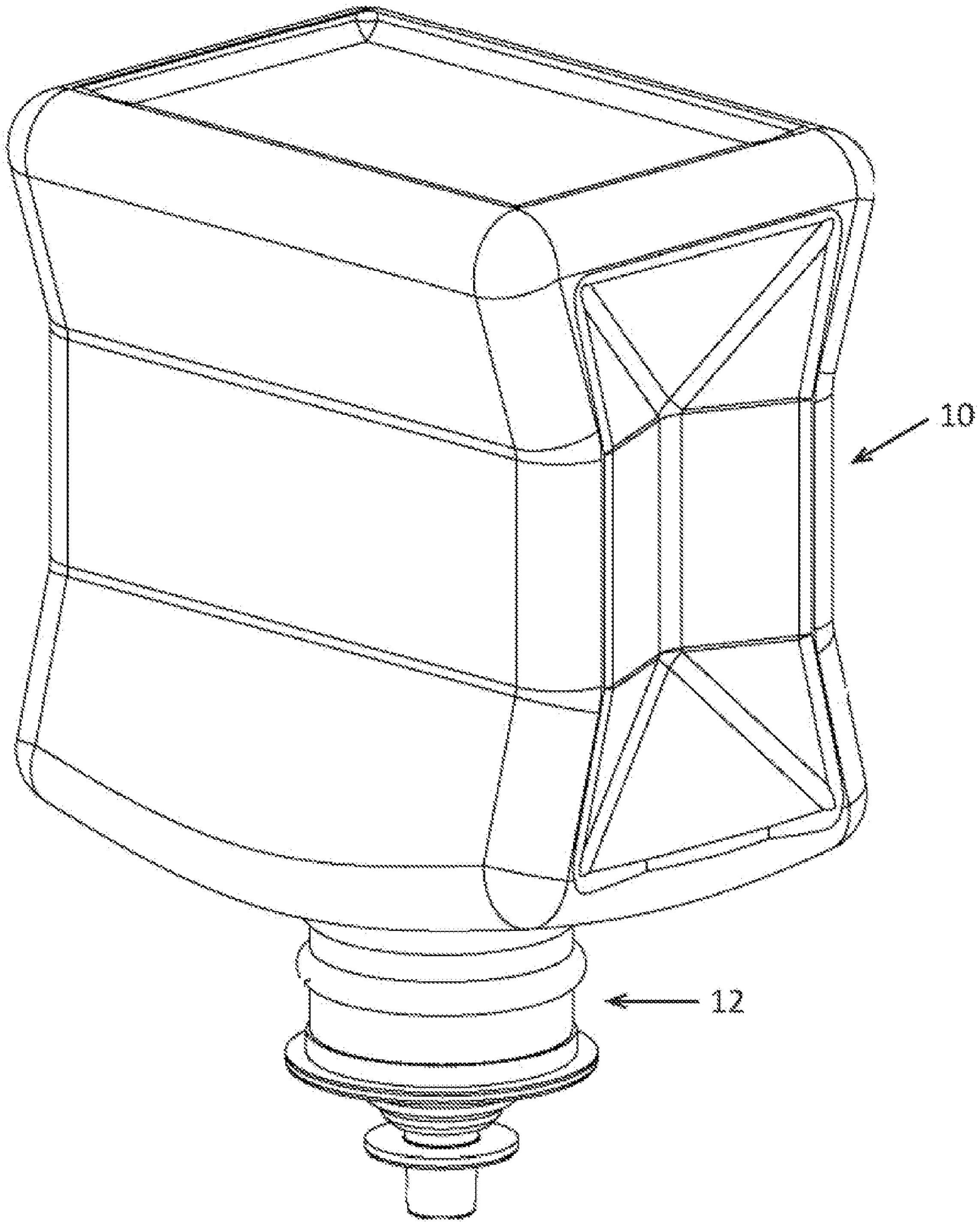
FIG. 2 shows a perspective view of a foam dispenser including a foaming assembly with a porous foaming element.
Figure 3:
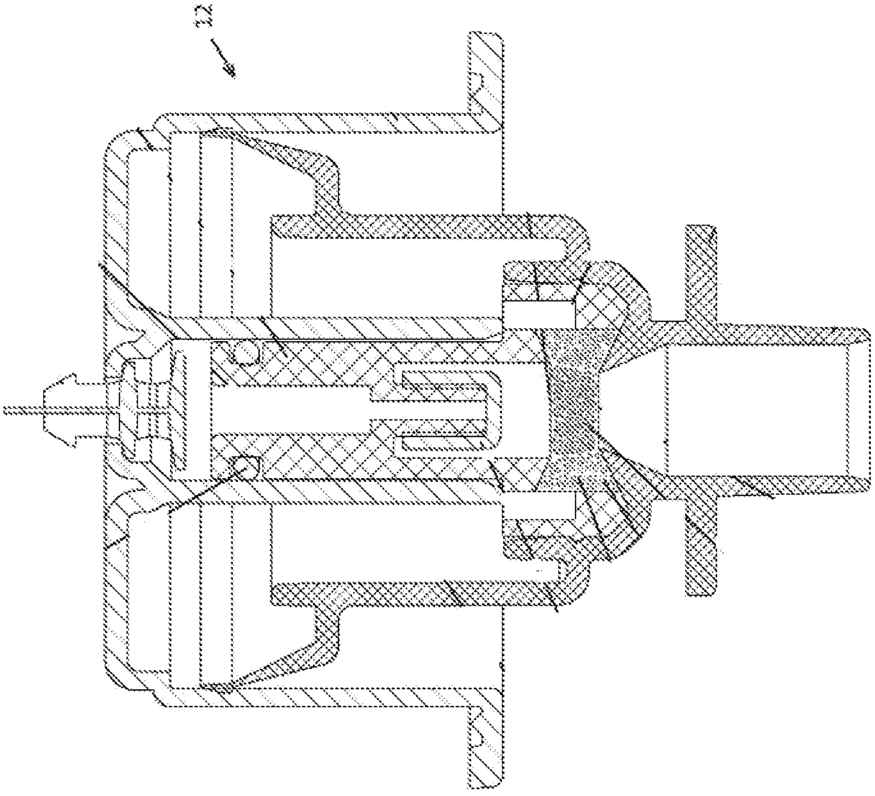
FIG. 3 shows a sectional view of the foaming assembly of FIG. 2.

The formulations described below were tested using upright foam pumps commercially available from Albea (Le Cignac, Gennevilliers, France). The inverted pumps (Optidose) are commercially available wall mounted dispensers obtainable from Deb Limited, United Kingdom.

Cleansing Performance

Cleansing performance was typically carried out using the following method:

The test model of the hand washing test with standardised soiling or paint gives information about the cleaning effect of the products to be tested. For relevance in practice, it is necessary that all subjects have a characteristic skin structure on the palms of the hands caused by manual work. Using one product at time, the following test is carried out in the morning and afternoon:

Test Procedure with Water:

- 0.5 g of soiling (model soiling, practice soiling or paint) is distributed on the palm and the back of the hand and rubbed in
- Leave to dry for 1½ min
- 1.2 g of cleansing composition are applied and rubbed in
- 1 ml of water is added and wash for 30 s
- Add a further 1 ml of water and wash for 30 s
- Rinse under cold running water
- Visual assessment of the residual soiling (RS) on the back of the hand and the palm according to the scale, see below.

Test Procedure without Water:

- 0.5 g of soiling (model soiling, practice soiling or paint) are distributed on the palm and on the back of the hand and rubbed in
- Leave to dry for 1½ min
- 1.2 g of cleaning composition are applied and rubbed in
- Using a cellulose paper, the soiling on the hand surfaces is removed together with the product
- Visual assessment of the residual soiling (RS) on the back of the hand and the palm according to the scale, see below.
- 0=clean 5=no cleaning effect (graduation in steps of 0.5 possible).

The percentage cleaning effect is calculated according to the following formula:

$$\text{cleaning effect [\%]} = \frac{10 - \left(\overline{RS}_{palm} + \overline{RS}_{back}\right)}{10} * 100\%$$

$RS_{palm}$=mean value of the residual soiling on palms of n measurement series (subjects).

$RS_{back}$=mean value of the residual soiling on backs of hands of n measurement series (subjects).

Since the deterioration of the cleaning effect has a broader variation range, an absolute deviation of 5% between two measurement series is allowable.

Composition of a suitable model soiling:

Flame soot: 5.42%

Iron oxide ($Fe_2O_3$): 0.72%

Comparative Example 1

The prior art formulation Sasol number 11574.

| Formulation Sasol No. 11574 Mild and Caring Shower Foam | | Z1 |
|---|---|---|
| raw materials | INCI | % |
| Marlowet CG | PEG-18 Castor Oil Dioleate | 1.00 |
| Marlinat 242/90 MC | MIPA Laureth Sulfate (and) Propylen Glycol | 12.00 |
| Sunflower Oil | Helianthus Annus Seed Oil | 1.00 |
| Cosmacol ELI | C12-13 Alkyl Lactate | 0.30 |
| Antil 200 | PEG 200 Hydrogenated Glyceryl Palmate (and) PEG-7 Glyceryl Cocoate | 0.20 |
| NaCl | Sodium Chloride | 2.00 |
| Cocoamidopropyl Betaine (38% active) | Cocoamidopropylbetaine | 5.00 |
| Preservative | | q.s. |
| Lactic acid | Lactic acid | q.s. |
| Perfume | Parfum/Fragrance | q.s. |
| D-Panthenol 75 L | Panthenol | q.s. |
| Water | Water | add to 100 |
| WAS content in % | | 12.70 |
| Total | | 100.000 |
| Cleansing Performance | | 49% |
| Foam Quality Optidose 7:1 air/product ratio upside down | | − |
| Foam Quality Albea Pump 7:1 air/product ratio bottom up | | ++ |

Sasol Formulation 11574 is a mild and caring shower foam composition, comprising oil and is similar to the intended final product the inventors were trying to identify. Using the conventional upright Albea foam, it was possible to foam the formulation. However, the inverted Optidose pump was unable to produce foam.

Comparative Example 2

| Formulation Clariant All/4063 Luxurious Foam Essence Facial Cleanser | | Z2 |
|---|---|---|
| raw materials | INCI | % |
| Genapol LRO liq. | Sodium Laureth Sulfate | 14.800 |
| GlucoTain Care | Cocoyl Methyl Glucamide | 5.000 |
| GlucoTain Clear | Capryloyl/Caproyl Methyl Glucamide | 2.000 |
| NaCl | Sodium Chloride | 2.000 |
| Preservative | Sodium Benzoate | q.s. |
| Citric Acid 50% | Citric Acid | q.s. |
| Perfume | Parfum/Fragrance | q.s. |
| Water | Water | add to 100 |
| WAS content in % | | 7.99 |
| Total | | 100.000 |
| Cleansing Performance | | 55% |
| Foam Quality Optidose 7:1 air/product ratio upside down | | – |
| Foam Quality Albea Pump 7:1 air/product ratio bottom up | | +++ |

Comparative Examples 2 shows a non-oil based cleanser, containing fatty acid alkyl glucamides. Again, that formulation was able to be foamed using upright foamers, but was unable to produce foams using inverted foaming devices and it has got also not a suitable cleansing performance.

On identifying the problem with using inverted foamers, the Applicant tried a number of different types of additives to try and produce a satisfactory composition that produced foaming in both the uprights and inverted pumps. These included:

Nonionics like Fatty alcohol ethoxylates such as Polyethylene glycol ethers of tridecyl alcohol, which have a good cleaning efficacy but inhibit the foam quality. Various trials with fatty alcohol ethoxylates to stabilise the foam failed.

To improve the foaming in combination with the cleansing properties. The Applicant also tried laureth-6 carboxylic acid and MIPA laureth sulfate. Alkylpolyglucose, disodium laureth sulfosuccinate, laureth-10, sodium cocoamphopropionate and N,N-dimethyl 9-decenamide were tried as alternatives but also failed.

A change from polyethylene glycol ethers to methyl glucamides (such as capryloyl/caproyl methyl glucamide, lauroyl/myristoyl methyl glucamide, cocoyl methyl glucamide) showed at least the beneficial effect while foaming and giving a good cleansing performance.

TABLE 1

| raw materials | INCI | Aa1 [%] | Bb1 [%] | Bb2 [%] | Bb3 [%] | Cc1 [%] | Ct2 [%] | Dd1 [%] | Dd2 [%] | Dd3 [%] | Ee1 [%] |
|---|---|---|---|---|---|---|---|---|---|---|---|
| Marlowet CG | PEG-18 Castor Oil Dioleate | 2 | 2 | 2 | 2 | 2 | 1.6 | 2 | 2 | 2 | 2 |
| Tegosoft M | Isopropyl Myristate | 2 | 2 | 2 | 2 | 2 | 2 | 2 | 2 | 2 | 2 |
| Tegosoft OS | Ethylhexyl Stearate | 3 | 3 | 3 | 3 | 3 | 3 | 3 | 3 | 3 | 3 |
| Tegosoft GC | PEG-7 Glyceryl Cocoate | 7 | 7 | 7 | 7 | 7 | 7 | 7 | 7 | 7 | 7 |
| SLES, preserved 28% | Sodium Laureth Sulfate | 30 | 30 | 30 | 30 | 25 | 32 | 30 | 30 | 30 | 30 |
| Tego Betain 810 35% | Capryl/Capamido-propyl Betaine | 5 | 5 | 5 | 5 | | 5 | 5 | 5 | 5 | |
| Trideceth-7 | Trideceth-7 | 4 | 4 | 4 | 4 | 4 | 4 | 4 | 4 | 3 | 4 |
| Barlox 12 | Cocoamine Oxide | | 3 | 2 | 1 | | | | | | |
| Benecel F50 | Hydroxypropylmethyl Cellulose | | | | | | | 0.3 | | | |
| Benecel E50 | Hydroxypropylmethyl Cellulose | | | | | | | | 0.3 | | |
| Stepen Mild LSB 25% | Sodium Lauryl/ Sufoacetate/ Disodium Laureth Sulfosuccinate | | | | | | | | | 1 | 10 |
| Mackamine LA 31% | Lauramine Oxide | | | | | | | | | | 3 |
| 1,3-Butandiol rein | Butylene Glycol | | | | | | | | | | |
| Antil 200 | PEG-200 Hydrogenated Glyceryl Palmate, PEG-7 Glyceryl Cocoate | | | | | | | | | | |
| Tegosoft LSE 65 K soft | Sucrose Cocoate | | | | | | | | | | |
| Natriumbenzoat Typ 2 | Sodium Benzoate | q.s. | q.s. | q.s. | q.s. | q.s. | q.s. | q.s. | q.s. | q.s. | q.s. |
| Citric Acid | Citric Acid | q.s. | q.s. | q.s. | q.s. | q.s. | q.s. | q.s. | q.s. | q.s. | q.s. |
| Water | Water | add to 100 | add to 100 | add to 100 | add to 100 | add to 100 | add to 100 | add to 100 | add to 100 | add to 100 | add to 100 |

TABLE 1-continued

| | | | | | | | | | | | |
|---|---|---|---|---|---|---|---|---|---|---|---|
| WAS content in % | | 14.15 | 17.15 | 16.15 | 15.15 | 11.00 | 14.71 | 14.15 | 14.15 | 13.40 | 15.50 |
| Total | | 100.00 | 100.00 | 100.00 | 100.00 | 100.00 | 100.00 | 100.00 | 100.00 | 100.00 | 100.00 |
| Cleansing performance | | >75% | >75% | >75% | >75% | >75% | >75% | >75% | >75% | >75% | >75% |
| Foam Quality Optidose 7:1 air/product ratio upside down | | − | − | − | − | − | − | − | − | − | − |
| Foam Quality Albea Pump 7:1 air/product ratio bottom up | | +++ | +++ | +++ | +++ | +++ | +++ | +++ | +++ | +++ | +++ |

| raw materials | INCI | Ee2 [%] | Ff1 [%] | Ff2 [%] | Ff3 [%] | Gg1 [%] | Gg2 [%] | Gg3 [%] | Hh1 [%] | Hh2 [%] | Hh2 [%] |
|---|---|---|---|---|---|---|---|---|---|---|---|
| Marlowet CG | PEG-18 Castor Oil Dioleate | 2 | 2 | 2 | 2 | 2 | 2 | 2 | 2 | 2 | 2 |
| Tegosoft M | Isopropyl Myristate | 2 | 2 | 2 | 2 | 2 | 2 | 2 | 2 | 2 | 2 |
| Tegosoft OS | Ethylhexyl Stearate | 3 | 3 | 3 | 3 | 3 | 3 | 3 | 3 | 3 | 3 |
| Tegosoft GC | PEG-7 Glyceryl Cocoate | 7 | 7 | 7 | 7 | 7 | 7 | 7 | 7 | 7 | 7 |
| SLES, preserved 28% | Sodium Laureth Sulfate | 20 | 30 | 30 | 30 | 30 | 30 | 30 | 30 | 30 | 30 |
| Tego Betain 810 35% | Capryl/Capamido-propyl Betaine | | 5 | 5 | 5 | 5 | 5 | 5 | 5 | 5 | 5 |
| Trideceth-7 | Trideceth-7 | 1 | 4 | 4 | 4 | 4 | 4 | 4 | 4 | 4 | 4 |
| Barlox 12 | Cocoamine Oxide | | | | | | | | | | |
| Benecel F50 | Hydroxypropylmethyl Cellulose | | | | | | | | | | |
| Benecel E50 | Hydroxypropylmethyl Cellulose | | | | | | | | | | |
| Stepen Mild LSB 25% | Sodium Lauryl/ Sufoacetate/ Disodium Laureth Sulfosuccinate | 10 | | | | | | | | | |
| Mackamine LA 31% | Lauramine Oxide | 3 | 3 | 7 | 10 | | | | | | |
| 1,3-Butandiol rein | Butylene Glycol | | | | | 0.5 | 1 | 1.5 | | | |
| Antil 200 | PEG-200 Hydrogenated Glyceryl Palmate, PEG-7 Glyceryl Cocoate | | | | | | | | 1 | 2 | 3 |
| Tegosoft LSE 65 K soft | Sucrose Cocoate | | | | | | | | | | |
| Natriumbenzoat Typ 2 | Sodium Benzoate | q.s. | q.s. | q.s. | q.s. | q.s. | q.s. | q.s. | q.s. | q.s. | q.s. |
| Citric Acid | Citric Acid | q.s. | q.s. | q.s. | q.s. | q.s. | q.s. | q.s. | q.s. | q.s. | q.s. |
| Water | Water | add to 100 | add to 100 | add to 100 | add to 100 | add to 100 | add to 100 | add to 100 | add to 100 | add to 100 | add to 100 |
| WAS content in % | | 9.70 | 14.15 | 14.15 | 14.15 | 14.65 | 15.15 | 15.65 | 15.15 | 16.15 | 17.15 |
| Total | | 100.00 | 100.00 | 100.00 | 100.00 | 100.00 | 100.00 | 100.00 | 100.00 | 100.00 | 100.00 |
| Cleansing performance | | >75% | >75% | >75% | >75% | >75% | >75% | >75% | >75% | >75% | >75% |
| Foam Quality Optidose 7:1 air/product ratio upside down | | − | − | − | − | − | − | − | − | − | − |
| Foam Quality Albea Pump 7:1 air/product ratio bottom up | | +++ | +++ | +++ | +++ | +++ | +++ | +++ | +++ | +++ | +++ |

TABLE 2

| raw materials | INCI | Ii1 [%] | Ii2 [%] | Ii3 [%] | Ii4 [%] | Jj1 [%] | Jj2 [%] | Jj3 [%] | Jj4 [%] | Kk1 [%] | Kk2 [%] |
|---|---|---|---|---|---|---|---|---|---|---|---|
| Marlowet CG | PEG-18 Castor Oil Dioleate | 2 | 2 | 2 | 2 | 2 | 2 | 2 | 2 | 2 | 2 |
| Tegosoft M | Isopropyl Myristate | 2 | 2 | 2 | 5 | 2 | 2 | 2 | 2 | 2 | 2 |
| Tegosoft OS | Ethylhexyl Stearate | 2 | 1 | | | 3 | 3 | 3 | 3 | 3 | 3 |
| Tegosoft GC | PEG-7 Glyceryl Cocoate | 7 | 7 | 7 | 7 | 7 | 7 | 7 | 7 | 7 | 7 |
| SLES, preserved 28% | Sodium Laureth Sulfate | 30 | 30 | 30 | 30 | 20 | 15 | 20 | 10 | 30 | 30 |
| Tego Betain 810 35% | Capryl/Capamido-propyl Betaine | 6 | 7 | 8 | 5 | 15 | 20 | 5 | 5 | 5 | 5 |
| Trideceth-7 | Trideceth-7 | 4 | 4 | 4 | 4 | 4 | 4 | 4 | 4 | 4 | 4 |
| Tegosoft LSE 65 K soft | Sucrose Cocoate | 3 | 3 | 3 | 3 | 3 | 3 | 3 | 3 | | |
| Protelan LS 9011 | Sodium Lauroyl Sarcosinate | | | | | | | 10 | 20 | | |
| Elfan AT 84 G | Sodium Cocoyl Isethinoate | | | | | | | | | 1.5 | |
| Hostapon SCI 65 C | Sodium Cocoyl Isethionate, | | | | | | | | | | 1.5 |

TABLE 2-continued

| | | | | | | | | | | | |
|---|---|---|---|---|---|---|---|---|---|---|---|
| | Stearic Acid, Sodium Isethionate, Aqua | | | | | | | | | | |
| Rewoteric AM KSF 40 | Sodium Cocoampho-propionate | | | | | | | | | | |
| Dermofeel Sensolv | Isoamyl Laurate | | | | | | | | | | |
| Glycerin | Glycerin | | | | | | | | | | |
| Polyglykol 300 | PEG-5 | | | | | | | | | | |
| Polyglykol 400 | PEG-8 | | | | | | | | | | |
| Polyglykol 500 | PEG-12 | | | | | | | | | | |
| Propandiol 1,2 | Propylene Glycol | | | | | | | | | | |
| Natrinumbenzoat Typ 2 | Sodium Benzoate | q.s. | q.s. | q.s. | q.s. | q.s. | q.s. | q.s. | q.s. | q.s. | q.s. |
| Citric Acid | Citric Acid | q.s. | q.s. | q.s. | q.s. | q.s. | q.s. | q.s. | q.s. | q.s. | q.s. |
| Water | Water | add to 100 | add to 100 | add to 100 | add to 100 | add to 100 | add to 100 | add to 100 | add to 100 | add to 100 | add to 100 |
| WAS content in % | | 17.50 | 17.85 | 18.20 | 17.15 | 17.85 | 18.20 | 24.35 | 31.55 | 15.65 | 15.65 |
| Total | | 100.00 | 100.00 | 100.00 | 100.00 | 100.00 | 100.00 | 100.00 | 100.00 | 100.00 | 100.00 |
| Cleansing performance | | >75% | >75% | >75% | >75% | >75% | >75% | >75% | >75% | >75% | >75% |
| Foam Quality Optidose 7:1 air/product ratio upside down | | – | – | – | – | – | – | – | – | – | – |
| Foam Quality Albea Pump 7:1 air/product ratio bottom up | | +++ | +++ | +++ | +++ | +++ | +++ | +++ | +++ | +++ | +++ |

| raw materials | INCI | Ll1 [%] | Ll2 [%] | Mm1 [%] | Mm2 [%] | Mm3 [%] | Mm4 [%] | Nn1 [%] | Nn2 [%] | Nn3 [%] | Oo1 [%] |
|---|---|---|---|---|---|---|---|---|---|---|---|
| Marlowet CG | PEG-18 Castor Oil Dioleate | 2 | 2 | 2 | 2 | 2 | 2 | 2 | 2 | 2 | 2 |
| Tegosoft M | Isopropyl Myristate | 2 | 2 | 2 | 2 | 2 | 2 | 2 | 2 | 2 | 2 |
| Tegosoft OS | Ethylhexyl Stearate | 3 | 3 | 3 | 3 | 3 | 3 | 3 | 3 | 3 | 3 |
| Tegosoft GC | PEG-7 Glyceryl Cocoate | 7 | 7 | 7 | 7 | 7 | 7 | 7 | 7 | 7 | 7 |
| SLES, preserved 28% | Sodium Laureth Sulfate | 30 | 30 | 30 | 30 | 30 | 30 | 30 | 30 | 30 | 30 |
| Tego Betain 810 35% | Capryl/Capamido-propyl Betaine | | 5 | 5 | 5 | 5 | 5 | 6 | 6 | 6 | 6 |
| Trideceth-7 | Trideceth-7 | 4 | 2 | 4 | 4 | 4 | 4 | 4 | 4 | 4 | 4 |
| Tegosoft LSE 65 K soft | Sucrose Cocoate | | | | | | | | | | |
| Protelan LS 9011 | Sodium Lauroyl Sarcosinate | | | | | | | | | | |
| Elfan AT 84 G | Sodium Cocoyl Isethinoate | | | | | | | | | | |
| Hostapon SCI 65 C | Sodium Cocoyl Isethionate, Stearic Acid, Sodium Isethionate, Aqua | | | | | | | | | | |
| Rewoteric AM KSF 40 | Sodium Cocoampho-propionate | 5 | 2 | | | | | | | | |
| Dermofeel Sensolv | Isoamyl Laurate | | | 1 | | | | | | | |
| Glycerin | Glycerin | | | | 0.5 | 3 | 5 | | | | |
| Polyglykol 300 | PEG-5 | | | | | | | 0.5 | | | |
| Polyglykol 400 | PEG-8 | | | | | | | | 0.5 | | |
| Polyglykol 500 | PEG-12 | | | | | | | | | 0.5 | 0.2 |
| Propandiol 1,2 | Propylene Glycol | | | | | | | | | | |
| Natrinumbenzoat Typ 2 | Sodium Benzoate | q.s. | q.s. | q.s. | q.s. | q.s. | q.s. | q.s. | q.s. | q.s. | q.s. |
| Citric Acid | Citric Acid | q.s. | q.s. | q.s. | q.s. | q.s. | q.s. | q.s. | q.s. | q.s. | q.s. |
| Water | Water | add to 100 | add to 100 | add to 100 | add to 100 | add to 100 | add to 100 | add to 100 | add to 100 | add to 100 | add to 100 |
| WAS content in % | | 17.40 | 14.15 | 15.15 | 14.15 | 14.15 | 14.15 | 14.5 | 14.5 | 14.5 | 14.5 |
| Total | | 100.00 | 100.00 | 100.00 | 100.00 | 100.00 | 100.00 | 100.00 | 100.00 | 100.00 | 100.00 |
| Cleansing performance | | >75% | >75% | >75% | >75% | >75% | >75% | >75% | >75% | >75% | >75% |
| Foam Quality Optidose 7:1 air/product ratio upside down | | – | – | – | – | – | – | – | – | – | – |
| Foam Quality Albea Pump 7:1 air/product ratio bottom up | | +++ | +++ | +++ | +++ | +++ | +++ | +++ | +++ | +++ | +++ |

| raw materials | INCI | Oo2 [%] | Oo3 [%] | Pp1 [%] | Pp2 [%] | Pp3 [%] |
|---|---|---|---|---|---|---|
| Marlowet CG | PEG-18 Castor Oil Dioleate | 2 | 2 | 2 | 2 | 2 |
| Tegosoft M | Isopropyl Myristate | 2 | 2 | 2 | 2 | 2 |
| Tegosoft OS | Ethylhexyl Stearate | 3 | 3 | 3 | 3 | 3 |
| Tegosoft GC | PEG-7 Glyceryl Cocoate | 7 | 7 | 7 | 7 | 7 |
| SLES, preserved 28% | Sodium Laureth Sulfate | 30 | 30 | 30 | 30 | 30 |
| Tego Betain 810 35% | Capryl/Capamido-propyl Betaine | 6 | 6 | 6 | 6 | 6 |
| Trideceth-7 | Trideceth-7 | 4 | 4 | 4 | 4 | 4 |
| Tegosoft LSE 65 K soft | Sucrose Cocoate | | | | | |

TABLE 2-continued

| | | | | | | |
|---|---|---|---|---|---|---|
| Protelan LS 9011 | Sodium Lauroyl Sarcosinate | | | | | |
| Elfan AT 84 G | Sodium Cocoyl Isethinoate | | | | | |
| Hostapon SCI 65 C | Sodium Cocoyl Isethionate, Stearic Acid, Sodium Isethionate, Aqua | | | | | |
| Rewoteric AM KSF 40 | Sodium Cocoampho-propionate | | | | | |
| Dermofeel Sensolv | Isoamyl Laurate | | | | | |
| Glycerin | Glycerin | | | | | |
| Polyglykol 300 | PEG-5 | | | | | |
| Polyglykol 400 | PEG-8 | | | | | |
| Polyglykol 500 | PEG-12 | 3 | 5 | | | |
| Propandiol 1,2 | Propylene Glycol | | | 2 | 5 | 10 |
| Natrinumbenzoat Typ 2 | Sodium Benzoate | q.s. | q.s. | q.s. | q.s. | q.s. |
| Citric Acid | Citric Acid | q.s. | q.s. | q.s. | q.s. | q.s. |
| Water | Water | add to 100 | add to 100 | add to 100 | add to 100 | add to 100 |
| WAS content in % | | 14.5 | 14.5 | 14.5 | 14.5 | 14.5 |
| Total | | 100.00 | 100.00 | 100.00 | 100.00 | 100.00 |
| Cleansing performance | | >75% | >75% | >75% | >75% | >75% |
| Foam Quality Optidose 7:1 air/product ratio upside down | | – | – | – | – | – |
| Foam Quality Albea Pump 7:1 air/product ratio bottom up | | +++ | +++ | +++ | +++ | +++ |

TABLE 3

| raw materials | INCI | Qq1 [%] | Rr1 [%] | Rr2 [%] | Ss1 [%] | Ss2 [ %] | Ss3 [%] | Tt1 [%] | Tt2 [%] |
|---|---|---|---|---|---|---|---|---|---|
| Marlowet CG | PEG-18 Castor Oil Dioleate | 2 | 2 | 2 | 2 | 2 | 2 | 2 | 2 |
| Tegosoft M | Isopropyl Myristate | 2 | 2 | 2 | 2 | 2 | 2 | 2 | 2 |
| Tegosoft OS | Ethylhexyl Stearate | 3 | 3 | 3 | 3 | 3 | 3 | 3 | |
| Tegosoft GC | PEG-Glyceryl Cocoate | 7 | 7 | 7 | 7 | 7 | 7 | | |
| SLES, preserved 28% | Sodium Laureth Sulfate | 30 | 30 | 30 | 30 | 30 | 30 | 30 | 30 |
| Tego Betain 810 35% | Capryl/Capamidopropyl Betaine | 5 | 5 | 5 | 5 | 5 | 5 | 5 | 8 |
| Trideceth-7 | Trideceth-7 | | | | | | | | |
| Cremer Coore PG 4 Cocoate | Polyglyceryl-4 Cocoate | 4 | | | | | | | |
| Marlinat 242/90 M 90% | MIPA Laureth Sulfate, Propylene Glycol | | 4 | | | | | | |
| Akypo RLM 45 92% | Laureth-6 Carboxylic Acid | | | 4 | | | | | |
| Eucarol Age SS 45% | Disodium aikyipoly-glukosesulfosuccinate | | | | 4 | | | | |
| Lavoral WW hochkonz. | Laureth-10 | | | | | 4 | | | |
| Rewoteric AM KSF 40 | Sodium Cocoamphopropionate | | | | | | 5 | | |
| Steposol MET 10 U 97% | N,N-dimethyl 9-decenamide | | | | | | | 4 | 4 |
| Tegosoft PC31 | Polyglyceryl-3 Caprate | | | | | | | | |
| Gluco Tain Clear 50% | Capryloyl/Caproyl Methyl Glucamide | | | | | | | | |
| Gluco Tain Flex 35% | Lauroyl/Myristoyl Methyl Glucamide | | | | | | | | |
| Gluco Tain Care 40% | Cocoyl Methyl Glucamide | | | | | | | | |
| Betaine Coco Base 30% | Cocoamidopropylbetaine | | | | | | | | |
| Natriumbenzoat Typ 2 | Sodium Benzoate | q.s. | q.s. | q.s. | q.s. | q.s. | q.s. | q.s. | q.s. |
| Citric Acid | Citric Acid | q.s. | q.s. | q.s. | q.s. | q.s. | q.s. | q.s. | q.s. |
| Water | Water | add to 100 | add to 100 | add to 100 | add to 100 | add to 100 | add to 100 | add to 100 | add to 100 |
| WAS content in % | | 14.15 | 13.75 | 13.83 | 11.95 | 14.15 | 15.15 | 14.03 | 15.08 |
| Total | | 100.00 | 100.00 | 100.00 | 100.00 | 100.00 | 100.00 | 100.00 | 100.00 |
| Cleansing performance | | >70% | >70% | >70% | >70% | >70% | >70% | >70% | >70% |
| Foam Quality Optidose 7:1 air/product ratio upside down | | + | + | + | + | + | + | + | + |
| Foam Quality Albea Pump 7:1 air/product ratio bottom up | | +++ | +++ | +++ | +++ | +++ | +++ | +++ | +++ |

| raw materials | INCI | Tt3 [%] | Tt4 [%] | Uu1 [%] | Uu2 [%] | Uu3 [%] | Vv1 [%] | Vv2 [%] | Vv1 [%] |
|---|---|---|---|---|---|---|---|---|---|
| Marlowet CG | PEG-18 Castor Oil Dioleate | 2 | 2 | 2 | 2 | 2 | 2 | 2 | 2 |
| Tegosoft M | Isopropyl Myristate | 2 | 2 | 2 | 2 | 2 | 2 | 2 | 2 |
| Tegosoft OS | Ethylhexyl Stearate | | | 3 | 3 | 3 | | | |
| Tegosoft GC | PEG-Glyceryl Cocoate | | | 7 | 7 | 7 | 7 | 7 | 7 |
| SLES, preserved 28% | Sodium Laureth Sulfate | 30 | 15 | 30 | 30 | 30 | 30 | 30 | 30 |
| Tego Betain 810 35% | Capryl/Capamidopropyl Betaine | 5 | 20 | 5 | 5 | 5 | 8 | 8 | |
| Trideceth-7 | Trideceth-7 | | | | | | | | |

TABLE 3-continued

| | | | | | | | | | |
|---|---|---|---|---|---|---|---|---|---|
| Cremer Coore PG 4 Cocoate | Polyglyceryl-4 Cocoate | | | | | | | | |
| Marlinat 242/90 M 90% | MIPA Laureth Sulfate, Propylene Glycol | | | | | | | | |
| Akypo RLM 45 92% | Laureth-6 Carboxylic Acid | | | | | | | | |
| Eucarol Age SS 45% | Disodium aikyipoly-glukosesulfosuccinate | | | | | | | | |
| Lavoral WW hochkonz. | Laureth-10 | | | | | | | | |
| Rewoteric AM KSF 40 | Sodium Cocoamphopropionate | | | | | | | | |
| Steposol MET 10 U 97% | N,N-dimethyl 9-decenamide | 4 | 4 | | | | | | |
| Tegosoft PC31 | Polyglyceryl-3 Caprate | 3 | 3 | | | | | | |
| Gluco Tain Clear 50% | Capryloyl/Caproyl Methyl Glucamide | | | 4 | | | 4 | 6 | |
| Gluco Tain Flex 35% | Lauroyl/Myristoyl Methyl Glucamide | | | | 4 | | | | |
| Gluco Tain Care 40% | Cocoyl Methyl Glucamide | | | | | 4 | 2 | | 4 |
| Betaine Coco Base 30% | Cocoamidopropylbetaine | | | | | | | | 8 |
| Natriumbenzoat Typ 2 | Sodium Benzoate | q.s. | q.s. | q.s. | q.s. | q.s. | q.s. | q.s. | q.s. |
| Citric Acid | Citric Acid | q.s. | q.s. | q.s. | q.s. | q.s. | q.s. | q.s. | q.s. |
| Water | Water | add to 100 | add to 100 | add to 100 | add to 100 | add to 100 | add to 100 | add to 100 | add to 100 |
| WAS content in % | | 14.03 | 15.08 | 12.15 | 11.55 | 11.75 | 14.00 | 14.20 | 12.40 |
| Total | | 100.00 | 100.00 | 100.00 | 100.00 | 100.00 | 100.00 | 100.00 | 100.00 |
| Cleansing performance | | >70% | >70% | >70% | >70% | >70% | >70% | >70% | >70% |
| Foam Quality Optidose 7:1 air/product ratio upside down | | + | + | ++ | ++ | ++ | +++ | +++ | +++ |
| Foam Quality Albea Pump 7:1 air/product ratio bottom up | | +++ | +++ | +++ | +++ | +++ | +++ | +++ | +++ |

TABLE 4

| raw materials | INCI | A1 [%] | A2 [%] | A3 [%] | A4 [%] | B1 [%] | B2 [%] | C1 [%] |
|---|---|---|---|---|---|---|---|---|
| Marlowet CG | PEG-18 Castor Oil Dioleate | 2.000 | 2.000 | 2.000 | 2.000 | 2.000 | 2.000 | 2.000 |
| Tegosoft M | Isopropyl Myristate | 2.000 | 2.000 | 2.000 | 2.000 | 2.000 | 2.000 | 3.000 |
| Tegosoft P | Isopropyl Palmitate | | | | | | | |
| Tegosoft GC | PEG-7 Glyceryl Cocoate | 7.000 | 7.000 | 7.000 | 7.000 | 7.000 | 7.000 | 7.000 |
| SLES, preserved 28% | Sodium Laureth Sulfate | 30.000 | 30.000 | 30.000 | 30.000 | 30.000 | 40.000 | 30.000 |
| Gluco Tain Care 55% | Cocoyl Methyl Glucamide | 1.000 | 2.000 | 3.000 | 5.000 | 10.000 | 10.000 | 3.000 |
| Betaine Coco Base (30%) | Cocoamidopropylbetaine | 10.000 | 9.000 | 9.000 | 9.000 | 9.000 | 9.000 | 9.000 |
| Natriumbenzoat Typ 2 | Sodium Benzoate | q.s. | q.s. | q.s. | q.s. | q.s. | q.s. | q.s. |
| Citric Acid | Citric Acid | q.s | q.s | q.s | q.s | q.s | q.s. | q.s |
| Water | Water | add to 100 | add to 100 | add to 100 | add to 100 | add to 100 | add to 100 | add to 100 |
| WAS content in % | | 11.950 | 12.200 | 12.750 | 13.850 | 16.600 | 19.400 | 12.750 |
| Total | | 100 | 100 | 100 | 100 | 100 | 100 | 100 |
| Cleansing Performance | | >70% | >70% | >70% | >70% | >70% | >70% | >70% |
| Foam Quality Optidose 7:1 air/product ratio upside down | | +++ | +++ | +++ | +++ | +++ | +++ | +++ |
| Foam Quality Albea Pump 7:1 air/product ratio bottom up | | +++ | +++ | +++ | +++ | +++ | +++ | +++ |

| raw materials | INCI | C2 [%] | D1 [%] | D2 [%] | E1 [%] | E2 [%] | F1 [%] | F2 [%] |
|---|---|---|---|---|---|---|---|---|
| Marlowet CG | PEG-18 Castor Oil Dioleate | 2.000 | 2.000 | 1.000 | 2.000 | 2.000 | 2.000 | 2.000 |
| Tegosoft M | Isopropyl Myristate | 1.000 | 2.000 | 1.000 | 2.000 | 2.000 | | |
| Tegosoft P | Isopropyl Palmitate | | | | | | 2.000 | 2.000 |
| Tegosoft GC | PEG-7 Glyceryl Cocoate | 7.000 | 7.000 | 7.000 | 7.000 | 7.000 | 7.000 | 7.000 |
| SLES, preserved 28% | Sodium Laureth Sulfate | 30.000 | 30.000 | 30.000 | 25.000 | 20.000 | 20.000 | 15.000 |
| Gluco Tain Care 55% | Cocoyl Methyl Glucamide | 3.000 | 10.000 | 10.000 | 3.000 | 3.000 | 3.000 | 3.000 |
| Betaine Coco Base (30%) | Cocoamidopropylbetaine | 9.000 | 9.000 | 9.000 | 15.000 | 20.000 | 10.000 | 5.000 |
| Natriumbenzoat Typ 2 | Sodium Benzoate | q.s. | q.s. | q.s. | q.s. | q.s. | q.s. | q.s. |
| Citric Acid | Citric Acid | q.s | q.s | q.s | q.s | q.s | q.s | q.s |
| Water | Water | add to 100 | add to 100 | add to 100 | add to 100 | add to 100 | add to 100 | add to 100 |
| WAS content in % | | 12.750 | 16.600 | 16.600 | 13.150 | 13.250 | 10.250 | 7.350 |
| Total | | 100 | 100 | 100 | 100 | 100 | 100 | 100 |
| Cleansing Performance | | >70% | >70% | >70% | >70% | >70% | 65% | 61% |
| Foam Quality Optidose 7:1 air/product ratio upside down | | +++ | +++ | +++ | +++ | +++ | +++ | +++ |
| Foam Quality Albea Pump 7:1 air/product ratio bottom up | | +++ | +++ | +++ | +++ | +++ | +++ | +++ |

Results show that combining oils with fatty acid alkyl glucamides produces formulations that may be used in both upright and inverted foaming pumps. Using alternative formulations without alkyl glucamides produces formulations with lower foam quality with inverted pumps.

FIG. 1 shows the mean cleaning efficacy of two formulations (Estesol Foam Pure and Estesol Foam) compared to two commercially available foaming compositions and two liquid cleansing compositions. The Estesol foams are both based on Formulation A3. Estesol foam has 0.2% by weight fragrance and 0.001% by weight of dye added with a reduction in the amount of water added.

Stephalen™ Flash Foam is available from Peter Greven Physioderm GmbH, Euskirchen,
Germany and comprises
Water,
Glycerin,
Sodium laureth sulfate,
PEG-7 glyceryl cocoate,
Cocamidopropyl betaine,
Sodium citrate,
Citric acid,
Sodium benzoate,
Potassium sorbate,
Perfume and
C.I. 42051

Refresh™ Azure Foam is available from Deb Limited, United Kingdom. It contains:
Aqua
Sodium laureth sulfate
Propylene glycol
Glycerin
PEG-7 glyceryl cocoate
Cocamidopropyl betaine
Parfum
Citric acid
2-Bromo-2-nitropropane-1,3-diol
Methylchloroisothiazolinone
Methylisothiazolinone
Magnesium nitrate
Magnesium chloride
CI 42090

Gojo™ Eco Soy™ is a liquid hand cleanser available from Gojo. It is an alcohol based hand cleanser and comprises:
Water
Ethoxylated branched C11-14, C13 rich alcohols
Fatty acids, soya Me esters
Polyoxyethylene tridecyl ether
Ethanol
Propylene glycol
Propan-2-ol Estesol Mild Wash is available from Deb Limited, United Kingdom and comprises:
Aqua
Sodium Laureth Sulfate
Sodium Chloride
Disodium Laureth Sulfosuccinate
Laureth-2
Sulfated Castor Oil
Glycol Distearate
Steareth-4
Poylquaternium-7
Citric Acid
PEG-30 Glyceryl Cocoate
Sodium Benzoate The figure shows that conventional foam products have lower cleaning efficacy than conventional liquid, unfoamed hand washes. The foaming compositions of the invention produce foams with a cleaning efficiency in excess of the conventional foaming compositions and in excess of or comparable to liquid cleaning compositions.

The invention claimed is:

1. A dispensing system comprising: an inverted foam dispenser and a cleansing composition wherein the cleansing composition comprises:
a) 0.1 to 5% by weight of at least one emulsifier selected from PEG-18 castor dioleate, polyglycerine 4-caproate, PEG-10 glyceryl dioleate, glycereth-7 caprylate/caprate, or mixtures thereof;
b) 0.5 to 7% by weight of at least one oil;
c) 0 to 10% by weight of at least one hydrophobic emollient;
d) 5 to 20% by weight of at least one surfactant used as a soiling remover;
e) 0.5 to 12% by weight of at least one fatty acid glucamide;
f) 1 to 8% by weight of at least one surfactant used as a foamer;
g) 0 to 1% by weight of at least one preservative;
h) 0 to 1% by weight of a pH modifier;
i) 0 to 10% by weight of one or more auxiliaries or additives;
j) water to make up 100% by weight.

2. The dispensing system of claim 1, wherein the composition comprises 1 to 5.5% by weight of fatty acid glucamide (e).

3. The dispensing system of claim 1, wherein the at least one fatty acid glucamide has a formula:

(1)

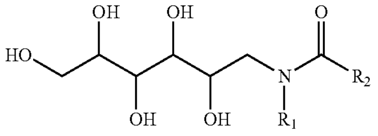

Where:
$R^1$=H or a C1 to C4 alkyl
$R^2$=$C_6$ to $C_{20}$ linear or branched, saturated or unsaturated hydrocarbon residue.

4. The dispensing system of claim 3, wherein $R_1$ is —H or —$CH_3$.

5. The dispensing system of claim 3 wherein $R_2$ is a $C_8$ to $C_{18}$ linear branched or unbranched, saturated or unsaturated hydrocarbon residue.

6. The dispensing system of claim 1, wherein the glucamide (e) comprises a mixture selected from caprylroyl/caproyl methyl glucamide, lauroyl/myristoyl methyl glucamide; or cocoyl methyl glucamide.

7. The dispensing system of claim 1, wherein the glucamide (e) is cocoyl methyl glucamide.

8. The dispensing system of claim 1, wherein the oil (b) is an isopropyl or ethyl hexyl fatty acid ester or alkyl benzoate.

9. The dispensing system of claim 8, wherein the oil (b) is selected from ethylhexyl stearate, isopropyl myristate, isopropyl palmitate, isopropyl stearate, isopropyl esters of rape seed oil or mixtures thereof.

10. The dispensing system of claim 1, wherein the composition comprises 1 to 3% by weight of the oil (b).

11. The dispensing system of claim 1, wherein the foamer is selected from cocamidopropyl betaine, capryl/capamido propyl betaine, fatty alcohol ether carboxylic acids and carboxylates, alkanol amides, amine oxides or ethoxylated alkyl sulfosuccinates.

12. The dispensing system of claim 1, the composition comprising 1 to 3% by weight of the emulsifier (a).

13. The dispensing system of claim 1, the composition comprising PEG-7 glyceryl cocoate, polyglyceryl-3-caprate, polyglycerine 4 caprate, glycereth-2 cocoate, or PEG-6 caprylic/capric glycerides as the emollient (c).

14. The dispensing system of claim 1, wherein the composition comprises 8 to 15% by weight of anionic surfactant (d).

15. The dispensing system of claim 1, the composition, comprising 2 to 5% by weight of foamer (f).

16. The dispensing system of claim 1, wherein washing active substances which are components d), e), and f) comprise 7-20% of the total weight of the composition.

17. A method of producing a foam, comprising providing a composition in a dispensing system of claim 1 and operating the dispenser to generate the foam.

* * * * *